(12) United States Patent
Muller et al.

(10) Patent No.: US 8,052,605 B2
(45) Date of Patent: Nov. 8, 2011

(54) MULTIMODAL CATHETER SYSTEM AND METHOD FOR INTRAVASCULAR ANALYSIS

(75) Inventors: James E. Muller, Auburndale, MA (US); Mark A. Wilder, Lexington, MA (US)

(73) Assignee: InfraReDx, Burlington, MA (US)

( * ) Notice: Subject to any disclaimer, the term of this patent is extended or adjusted under 35 U.S.C. 154(b) by 308 days.

(21) Appl. No.: 12/437,022

(22) Filed: May 7, 2009

(65) Prior Publication Data
US 2009/0299195 A1 Dec. 3, 2009

Related U.S. Application Data

(60) Provisional application No. 61/051,227, filed on May 7, 2008.

(51) Int. Cl.
*A61B 8/00* (2006.01)

(52) U.S. Cl. ........ 600/439; 600/462; 600/463; 600/467; 600/459; 600/454; 604/22; 604/523; 606/130; 606/159

(58) Field of Classification Search ............. 600/462, 600/463, 439, 467, 459, 454, 450, 471; 604/22, 604/523; 606/159
See application file for complete search history.

(56) References Cited

U.S. PATENT DOCUMENTS

| | | | |
|---|---|---|---|
| 5,773,835 A | 6/1998 | Sinofsky | |
| 5,916,210 A | 6/1999 | Winston | |
| 5,928,145 A | 7/1999 | Ocali et al. | |
| 6,016,440 A | 1/2000 | Simon et al. | |
| 6,134,003 A | 10/2000 | Tearney et al. | |
| 6,296,608 B1 | 10/2001 | Daniels et al. | |
| 6,409,672 B2 | 6/2002 | Webler et al. | |
| 6,501,551 B1 * | 12/2002 | Tearney et al. | 356/477 |
| 6,690,958 B1 | 2/2004 | Walker et al. | |
| 6,697,666 B1 | 2/2004 | Richards-Kortum | |
| 6,949,072 B2 | 9/2005 | Furnish et al. | |
| 6,986,739 B2 | 1/2006 | Warren et al. | |
| 7,289,842 B2 | 10/2007 | Maschke | |
| 7,450,241 B2 | 11/2008 | Zuluaga | |
| 7,860,555 B2 | 12/2010 | Saadat | |
| 2003/0028114 A1 | 2/2003 | Casscells, III et al. | |
| 2003/0109868 A1 | 6/2003 | Chin et al. | |
| 2003/0199747 A1 | 10/2003 | Michlitsch et al. | |
| 2003/0236443 A1 | 12/2003 | Cespedes et al. | |
| 2004/0024298 A1 | 2/2004 | Marshik-Guerts et al. | |
| 2005/0075574 A1 * | 4/2005 | Furnish et al. | 600/467 |

(Continued)

FOREIGN PATENT DOCUMENTS

WO  WO 97/32182 A1  9/1997

(Continued)

OTHER PUBLICATIONS

PCT International Search Report, issued in PCT/US2009/043119 on Aug. 27, 2009, 4 pages.

(Continued)

*Primary Examiner* — Brian Casler
*Assistant Examiner* — Joel Lamprecht
(74) *Attorney, Agent, or Firm* — Rothwell, Figg, Ernst & Manbeck, PC

(57) ABSTRACT

Methods, apparatus, and systems for intravascular analysis combine at least three analytical modalities. In one implementation, intravascular ultrasound, optical coherence tomography, and near infrared spectroscopy are combined to enable detection of multiple, different abnormalities in the arterial morphology during a single intravascular procedure.

14 Claims, 5 Drawing Sheets

U.S. PATENT DOCUMENTS

| | | |
|---|---|---|
| 2005/0101859 A1 | 5/2005 | Maschke |
| 2005/0113685 A1 | 5/2005 | Maschke et al. |
| 2005/0228295 A1 | 10/2005 | Tan |
| 2006/0100529 A1 | 5/2006 | Rueckmann et al. |
| 2006/0132790 A1 | 6/2006 | Gutin |
| 2006/0173284 A1 | 8/2006 | Ackerman et al. |
| 2006/0184048 A1 | 8/2006 | Saadat |
| 2007/0066890 A1 | 3/2007 | Maschke |
| 2007/0135887 A1* | 6/2007 | Maschke ..................... 623/1.11 |
| 2008/0097223 A1 | 4/2008 | Strickler et al. |
| 2008/0177145 A1 | 7/2008 | Furnish |
| 2009/0203991 A1 | 8/2009 | Papaioannou et al. |
| 2009/0253989 A1 | 10/2009 | Caplan et al. |

FOREIGN PATENT DOCUMENTS

| | | |
|---|---|---|
| WO | WO 03/057040 A1 | 7/2003 |
| WO | WO 03/088817 A2 | 10/2003 |
| WO | WO 2007/123518 A1 | 11/2007 |
| WO | WO 2008/057573 A2 | 5/2008 |

OTHER PUBLICATIONS

Tumlinson, A. et al., "Miniature Endoscope for Simultaneous Optical Coherence Tomography and Laser-Induced Fluorescence Measurement," *Applied Optics*, Optical Society of America, 43(1):113-121, (Jan. 1, 2004).

* cited by examiner

MULTIMODAL CATHETER SYSTEM AND METHOD FOR INTRAVASCULAR ANALYSIS

PRIORITY CLAIM

This application claims the benefit under 35 U.S. C 119(e) of U.S. Provisional Application Ser. No. 61/051,227, filed May 7, 2008, the disclosure of which is hereby incorporated by reference.

BACKGROUND

Atherosclerosis is a vascular disease characterized by the modification of the walls of blood carrying vessels. This modification can take the form of thickening of the vessel wall, eventually forming what are commonly referred to as "plaques." The mechanisms corresponding to the formation, progression, stabilization, or rupture of these plaques and their effects on humans has been an area of intense research in intravascular medicine. With the advent of interventional cardiology and percutaneous diagnostic and treatment procedures, the patient with coronary atherosclerotic disease was no longer required to automatically submit to coronary bypass surgery—an extremely invasive procedure with attendant risks and extended recovery time. Coronary stents were developed to revascularize narrowed (stenosed) vessels and millions of theses devices have been placed in patients worldwide. However, current statistics show that, while patient comfort and quality of life has been improved, treatment of coronary atherosclerotic disease by stenting has not significantly reduced the patient mortality. Patients treated with stents are still dying suddenly of heart attack.

Much more is now known about coronary disease than even a decade ago, but there are still many questions to be answered. From retrospective autopsy studies on heart attack victims, it has been shown (ref Virmani) that there is often a portion of the coronary artery tree that is completely blocked by a thrombosis, or blood clot. The thrombosis is typically in the vicinity of a plaque in the vessel wall. Referred to as the "culprit lesion," it would be this blockage that would cut off the blood supply to a portion of the heart, resulting in death of heart muscle tissue and possibly death of the individual. Certain plaques contain material which, when it comes into contact with blood, causes thrombogenesis, or clot formation. These plaques seem to have formed a reservoir, or core, of thrombogenic material behind a layer of fibrous tissue ("cap"), analogous to an abscess. Through some process or set of processes, the integrity of the fibrous layer can become compromised, whereby blood can eventually come into contact with the thrombogenic core. This can be a sudden event, where the patient had no prior warning or even symptoms. If one categorizes plaques broadly as stable—where they may still progress slowly and eventually restrict the vessel—and unstable—those that can change their status rapidly, among the key questions is: "How can we tell the difference?"

Historically, the search for atherosclerotic disease has been a search for the narrowing in the opening or "lumen" of the vessel. Angiography is one of the oldest intravascular technologies employed for this purpose. The technique typically employs a catheter, introduced percutaneously into the vasculature, that is used to inject a contrast agent, consisting of a radio opaque dye, into the blood vessels of interest. Using x-rays, a two dimensional live (cine) or still image of the vasculature can be obtained. The vessel lumen is visible wherever the contrast agent is able to flow. From these images, one can determine the size of the lumen and the presence of any narrowing or blockage. The presence of a plaque can sometimes be inferred by a diffuse lumen boundary. Despite being standard of care for many years and forming the basis for most therapy decisions, angiography alone suffers from some limitations. First, vessel narrowing is not necessarily rotationally isotropic. With only a single view angle from which to form the 2-D image, areas of narrowing can be underestimated or missed entirely. To obtain images from multiple viewpoints requires more time and exposure of the patient to contrast and x-rays. The nature of the image as a "lumenogram," along with limited spatial resolution, make it difficult, if not impossible, to make any statement about the characteristics of the tissue in the vessel wall. For example, it is impossible to distinguish between a fibrotic plaque and one with a necrotic, lipid filled core.

Intravascular ultrasound (IVUS) has emerged, in the last 15 years, as an imaging technology to measure tissue structural characteristics, in particular for blood vessels. IVUS employs a specially designed catheter, with an acoustic transducer at the distal tip, to send and receive ultrasonic signals. So called, "mechanical" IVUS catheters consist of a flexible polymer outer sheath, inside of which is a core that rotates and pulls back through the vessel, generating a series of circumferential scans of the vessel wall. The core typically consists of an RF transmission line, connecting the transducer at the distal tip to drive and receive electronics. A helically wound wire cable is typically used to transmit torque from a rotary motor, through the core to the distal tip, to ensure rotation of the tip with consistent angular velocity. Ultrasonic waves are back scattered by human tissue. The strength of the back scatter is a function of tissue properties, including density. The signal returning from tissue from a rotating IVUS catheter can be represented as a radar plot with a 360 degree view of a section of the vessel and the radial dimension showing the strength of the signal return as a function of distance from the center of the catheter. An advantage of IVUS is that it allows one to obtain an image of the inner walls of the vessel, even through intervening blood. With axial image resolution of 100-200 microns and imaging depth of greater than 5 mm, various structures within the vessel wall can be visualized, including areas of calcification and thickening of the arterial wall. Also, the boundary between the lumen and the vessel intima as well as that between the media and the adventitia can be visualized with accuracy good enough to calculate lumen dimensions and the area of plaques, or "plaque burden."

Optical coherence tomography (OCT) is an emerging technology that also provides structural information similar to IVUS. OCT depends on the scattering of light by tissue and uses the coherence properties of light, for example, using a Michelson interferometer, to determine the distance at which a scattering event occurred. The technique is similar to IVUS in that a catheter is moved over a guidewire into the blood vessel to a region of interest and then the core of the catheter is pulled back to scan the artery. However, there are several key differences. For example, the OCT signal cannot penetrate blood, requiring that the blood be cleared from the area of the vessel being imaged. A variety of methods have been employed to accomplish this, the most promising and least dangerous to the patient being a non-occlusive flush, using a bolus of saline/contrast mix. This method provides several seconds in which to obtain an image of a vessel segment.

Another class of intravascular analysis systems uses chemical analysis modalities. These approaches generally rely on optical spectral analysis including near infrared (NIR), Raman, and fluorescence spectral analysis.

Near Infrared Spectroscopy (NIR or NIRS) is a technique, again using light in the near infrared region of the spectrum, intended not to image the physical structure of the artery, but the chemical constituents, specifically cholesterol, of the arterial wall. Unlike OCT, NIR can perform such measurement through blood. Operation of a NIR catheter is very similar to that of IVUS with regard to insertion into the patient and pullback and acquisition of data. The result is a two dimensional map of the cholesterol, or lipid, content of the artery.

NIRS utilizes an intravascular optical catheter which, similarly to IVUS, is driven by a pullback and rotation unit that simultaneously rotates the catheter head around its longitudinal axis while withdrawing the catheter head through the region of the blood vessel of interest.

During this pullback operation, the spectral response of the inner vessel walls is acquired in a raster scan operation. This provides a spatially-resolved spectroscopic analysis of the region of interest. The strategy is that by determining the spectroscopic response of blood vessel walls, the chemical constituents of those blood vessel walls can be determined by application of chemometric analysis, for example.

In Raman spectral analysis, the inner walls of the blood vessel are illuminated by a narrow band, such as laser, signal. The Raman spectral response is then detected. This response is generated by the inelastic collisions betweens photons and the chemical constituents in the blood vessel walls. This similarly produces chemical information for the vessel walls.

Hybrid IVUS/optical catheters have been proposed. For example, in U.S. Pat. No. 6,949,072, which in incorporated herein by this reference in its entirety, a "device for vulnerable plaque detection" is disclosed. Specifically, this patent is directed to intravascular probe that includes optical waveguides and ports for the near infrared analysis of the blood vessel walls while simultaneously including an ultrasound transducer in the probe in order to enable IVUS analysis of the blood vessel walls.

SUMMARY

Aspects of the invention relate to systems, methods, and apparatus for combining three or more intravascular analysis modalities—and thereby exploiting the different diagnostic information available from each modality—in a single intravascular procedure.

Thus, the present invention concerns multimodal intravascular analysis. In one embodiment, a single catheter combines multiple diagnostic modalities, such as 3, 4 or even 5 diagnostic modalities. In some examples, two or more of the diagnostic modalities are used simultaneously, even during the same pullback and rotation cycle. In other examples, the modalities are employed serially in separate pullback and rotation cycles.

In general, providing catheter systems that yield chemical information, such as from NIR, Raman, and/or fluorescence spectroscopic analysis, along with other information: lumen dimension (stenosis) and vessel dimension (positive remodeling) and cap thickness (a possible indicator of plaque vulnerability) from IVUS and OCT and fractional flow rate (FFR) from a flow wire, has the potential to increase the likelihood of a positive patient outcome.

For example, a catheter that combines NIR, IVUS, OCT and a flow wire, provides the physician with a much more comprehensive data set from which to formulate a therapy decision, including stenting, medical therapy, or referral to coronary artery bypass grafting (CABG).

A further consideration is the "fusing" of image data obtained from different modalities (e.g. angiography, NIR, OCT, IVUS) and the accurate spatial co-registration (longitudinal and rotational) of the images. Having one catheter that incorporates multiple invasive imaging modalities provides a fixed frame of reference that greatly facilitates co-registration, especially when the diagnostic modalities are employed during the same pullback and rotation cycle. Success here is further facilitated by including position detection capabilities in the catheter such as sensors that detect externally-generated signals, magnetic fields, or emitters that generate externally detected signals.

These and other features, aspects, and advantages of the present invention will become apparent to those skilled in the art after considering the following detailed description, appended claims and accompanying drawings.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION

While IVUS analysis provides valuable information regarding certain structural aspects of an arterial wall that enables the practitioner to identify gross structural abnormalities, such as stenosis and other forms of remodeling, IVUS suffers from a number of inherent limitations relevant to the objective of characterizing plaque composition. For this reason, efforts to extend the capability of IVUS to actual characterization of tissue type (e.g. calcific, fibrotic, necrotic) in an effort to differentiate types of plaques and better inform treatment have been largely unsuccessful. Among the inherent limitations of IVUS that limit its efficacy are that calcified regions block the propagation of IVUS radiation. It is not uncommon for a coronary plaque to be covered with a calcific cap, and therefore, such plaque may go undetected in an IVUS analysis. Also, softer plaques, which often contain lipids, are generally hypoechoic. Thus, it is from an absence of signal that one must infer the plaque composition. Use of a null signal to infer plaque properties is not ideal and can be subject to errors.

OCT, like IVUS, provides information regarding the structural aspects of the arterial wall but has the capability to generate images with up to ten times better resolution than IVUS. This now enables the visualization of structures which cannot be seen with IVUS. In particular, the thickness of the fibrous cap covering a plaque with a necrotic core can now be measured with high precision. However, OCT optical signals are severely attenuated by blood and also have limited penetration in tissue. Not only does this mean that it is necessary to clear blood from the vessel, as mentioned previously, but the imaging depth in tissue achievable with OCT is limited to approximately 1 mm.

NIRS, as described above, provides information regarding the chemical constitution of the artery to identify the, cholesterol, or lipids content of the artery.

The inventors have determined that the combination of at least these three diagnostic modalities can significantly enhance the efficacy of the intraluminal analysis. For example, by identifying a variety of arterial abnormalities, such as positive remodeling (best detectable by IVUS), thin caps (best detectable by OCT), and a necrotic core (best detectable by spectroscopy, e.g., NIR), the diagnostic accuracy can be significantly improved. Moreover, by combining at least these three modalities in a single system, apparatus, and method, these multiple informational components used in the diagnosis can be obtained in a single intravascular procedure.

Figure 1:
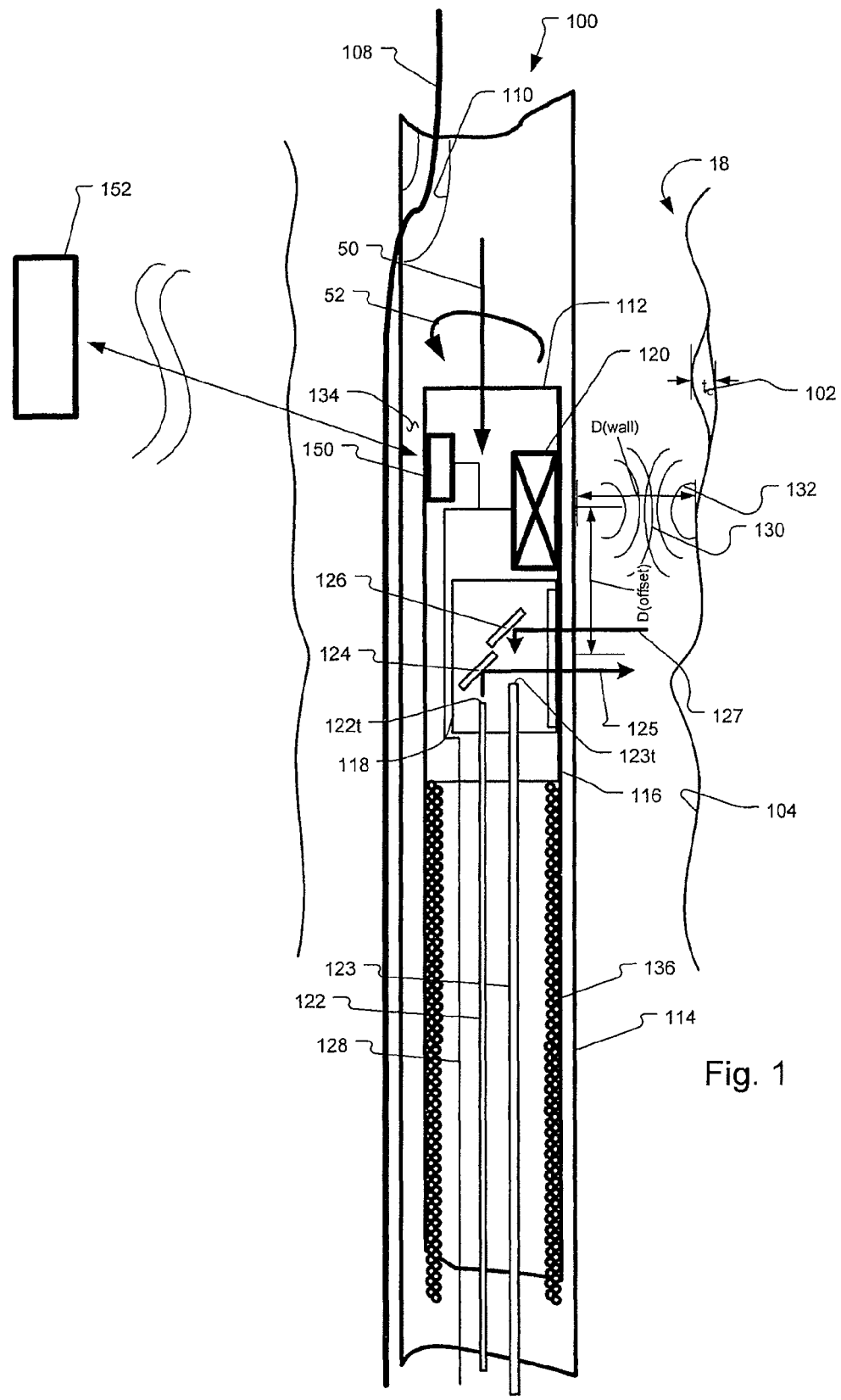
FIG. 1 is a cross-sectional view of an intravascular probe with a guidewire in a distal end of a catheter.

FIG. 1 shows an embodiment of an intravascular catheter system 100 that combines multiple diagnostic modalities.

In typical operation, the intravascular catheter 100 is advanced into a blood vessel 18 using a guidewire 108 that is threaded through the guidewire lumen 110.

The catheter system 100 further comprises an inner scanning catheter core 116 and outer sheath 114. The combination of the scanning catheter core 116 and sheath 114 enables the inner scanning catheter core 116 and specifically the catheter tip 112 to perform longitudinal translation (arrow 50) and rotation (arrow 52) while the sheath 114 prevents this movement from damaging the vessel 18 and specifically walls 104.

The tip 112 of the scanning catheter core 116 is located at the distal end of the catheter 100 and includes an optical bench 118 to transmit and receive light, typically infrared light, and an ultrasound transducer system 120 to transmit and receive ultrasound energy.

At least the distal end of the sheath 114 is composed of materials that are transparent to light, e.g., near infrared, employed by the optical diagnostic modalities (e.g., a polymer) and will also propagate ultrasound used by IVUS.

The optical bench 118 contains the terminations 122t, 123t of at least one delivery fiber 122 and at least one collection fiber 123, which extend between the proximal and distal ends of the catheter 100. Light 125 propagating through and emitted from the termination 122t of the delivery fiber 122 is redirected by a delivery mirror 124 towards the vessel, e.g., arterial, wall 104. A collection mirror 126 redirects light 127 scattered or reflected from various depths of the arterial wall 104 into a distal end 123t of the collection fiber 123.

In one implementation, a focusing element serves to collect the diverging optical beam from optical fiber 122 and refocus the beam into the vessel wall. Suitable focusing elements may include a gradient indexed lens, micro-optical lens, a grating or a curved mirror.

In an alternate implementation, a single fiber or fiber bundle may function as both a delivery and a collection waveguide.

In one implementation, the at least one delivery fiber 122 is a single mode optical fiber that propagates only a single spatial mode within the fiber at the wavelengths of interest. The collection fiber 123 is multimode fiber having a core diameter of approximately 60 micrometers or larger, including diameters to about 200 micrometers or larger. In one embodiment, the single mode delivery fiber is used with light generated by a tunable laser. In this embodiment, the delivery fiber is used to couple light both to the vessel walls 104 and back to the interferometer for OCT analysis. The large core of the collection fiber and higher numerical aperture improves collection efficiency for NIR, Raman, and/or fluorescence spectroscopic analysis. In an alternate implementation, other suitable sources of optical radiation, such as a super luminescent light-emitting diode ("SLED"), may be used instead of or in addition to the tunable laser.

The ultrasound transducer system 120 includes one or more transducers that direct ultrasound energy 130 towards the arterial wall 104 and receive ultrasound energy 132 reflected from the arterial wall 104. In one embodiment, the ultrasound transducer system is longitudinally adjacent to the optical bench 118. In an alternate implementation, the ultrasound system may be located at substantially the same longitudinal position as the distal end(s) of the delivering and collection fiber(s), offset from the fiber(s), for example, by 180 degrees. Using time multiplexing in one implementation, a single ultrasound transducer both generates the transmitted energy 130 and received reflected energy 132 into an electrical signal carried on wires 128. For example, during a first time interval, an electrical signal carried on wires 128 actuates the ultrasound transducer 120 to emit a corresponding ultrasound signal 130. Then during a second time interval, after the ultrasound signal 130 has reflected from the arterial wall 104, the ultrasound transducer 120 produces an electrical signal carried on wires 128. This electrical signal corresponds to the received ultrasound signal 132.

The received signal 132 is used by this IVUS analysis modality to determine the distance D(wall) between the head or distal end of the scanning catheter 112 and the vessel wall 104 and to determine the physical morphology, or structure, of the vessel wall itself. For example, the received signal 132 may be useful for characterizing atherosclerotic plaques, including plaque volume in the blood vessel wall and also the degree of stenosis of the blood vessels.

In other embodiments, the ultrasound signal is generated photo-acoustically by sending a light pulse through optical fiber 122 with enough energy to create an acoustic event that is detected by the ultrasound transducer system 120.

Between the sheath 114 and the core 116 is a transmission medium 134, such as saline or other fluid, surrounding the ultrasound transducer system 120 to facilitate acoustic transmission. The transmission medium 134 is also selected to be transparent to the near infrared light emitted from and received by the optical bench 118.

A torque cable 136 is attached to a scanning catheter core 116 and surrounds the optical fibers 122, 123 and the wires 128. This torque cable 136 transmits the torque from a pullback and rotation system through to the scanning catheter head 112. This feature enables the scanning catheter head 112 to rotate within sheath 114 to circumferentially scan the arterial wall 104 with light 125 and ultrasound energy 130.

In one embodiment, the catheter head 112 comprises an internal element 150 of a position detection system. The internal element 150 communicates with an external element 152, typically outside the patient's body, in order to determine the position of the catheter tip 112 relative to the external element 152. In one embodiment, the internal element is a sensor that detects a field, e.g., magnetic, generated by the external element 152. The detected position information is transmitted on wires 128 and is received by controller 300, as shown in FIG. 2.

In one embodiment, a position detection system developed by Mediguide Ltd. for guidewires and coronary catheterization devices could be used. The technology provides realtime position information. It uses a small sensor located in the device that is able to determine its position within a magnetic field created around the patient. In this way, additional position information is available, beyond that which would typically be provided from X-ray angiogram images.

Figure 2:
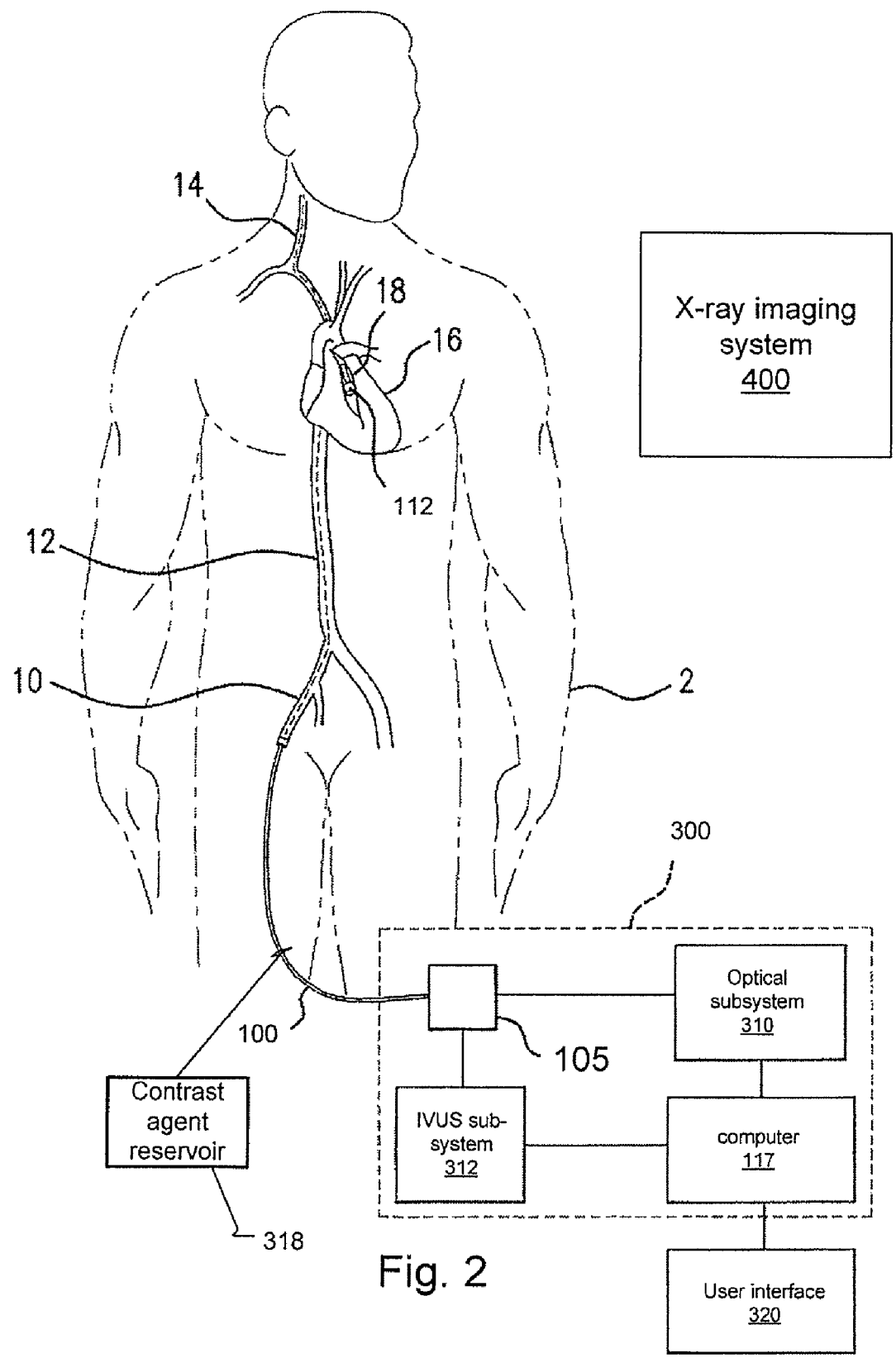
FIG. 2 is a schematic diagram illustrating the use of the catheter system and a system controller, according to the invention.

FIG. 2 illustrates an exemplary system for supporting multiple diagnostic catheter functions.

The system generally comprises the catheter 100, a controller 300, and a user interface 320.

In operation, first the guide wire and then the catheter 100 are inserted into the patient 2 via a guide catheter (not shown) already placed in a peripheral vessel, such as the femoral artery 10. The catheter tip 112 is then moved to a desired target region, such as a coronary artery 18 of the heart 16 or the carotid artery 14. This is achieved by moving the catheter 100 up through the aorta 12, riding on the guidewire 108.

When at the desired site, the pullback and rotation unit 105 is used both for the mechanical drive to the scanning catheter 112 and also to couple optical and electrical signals to and from the catheter 100. Specifically, the pullback and rotation unit 105 drives the scanning catheter core 116 to rotate and withdraw through the outer sheath 114. An exemplary pullback and rotation unit is disclosed in U.S. patent application Ser. No. 11/875,590, filed on Oct. 19, 2007, entitled Optical Catheter Carriage Interlock System and Method (U.S. Patent Application Pub. No. 2008-0097223), which is incorporated herein by this reference in its entirety. This disclosed pullback and rotation unit shows an optical layout in which the tunable signal from a tunable laser is coupled onto a rotating and translating drum via a rotary fiber optical joint (FORJ). Returning NIR signals are detected on the drum. Additional detectors are provided for common mode rejection of noise generated in the FORJ.

The IVUS subsystem 312 and the optical subsystem 310 are activated during each pullback cycle to generate appropriate signals for transmission through the catheter 100 and receive, detect, preprocess and digitize signals returned from the vessel walls 104. In a preferred embodiment, a tunable laser—or other suitable source of optical radiation—in the optical subsystem generates a narrowband optical signal that is wavelength scanned over a range in the NIR, covering one or more spectral bands of interest. The same or a different laser—or other suitable source of optical radiation—is used to generate signals for OCT analysis of the vessel walls. At the same time, the IVUS subsystem 312 is enabled to simultaneously generate ultrasound images of the vessel walls 104.

In one embodiment, the returning light is transmitted back down multimode collection fiber 123 of the catheter 100. The returning radiation is provided to the optical subsystem 310, which can comprise one or multiple optical detectors or spectrometers. Light returning on delivery fiber 122 is also analyzed, for example in an interferometer, in order to perform OCT analysis.

The optical analysis subsystem 310 collects, preprocesses, digitizes and passes raw spectral and OCT to the computer 117 for further processing, analysis and display information to the user interface 320.

The IVUS subsystem 312 collects, preprocesses, digitizes and passes the information from the ultrasound transducer 120 to the computer 117 for further processing, analysis and display formation to the user interface 320.

In more detail, the IVUS subsystem 312 comprises the drive electronics for driving the ultrasound transducer 120 and analyzing the response of the transducer 120 to determine the structural measure of interest in an IVUS-type system.

Generally, the computer 117 receives preprocessed, digitized raw IVUS, OCT and NIR data, performs additional processing, scan conversion and data registration and presents one or more representations of the morphological and chemical structure of the vessel walls to the operator via interface 320, as images and/or data maps. The computer 117 may combine the structural analysis information from the IVUS subsystem 312 with information from the optical analysis subsystem 310. For example, information from both systems is combined into hybrid images displayed to the operator on user interface 320. In further examples, the information from the IVUS and/or OCT analysis is used to improve the NIR analysis as described in U.S. application Ser. No. 12/062,188, filed Apr. 3, 2008, entitled: System and Method for Intravascular Structural Analysis Compensation of Chemical Analysis Modality, which is incorporated herein by this reference in its entirety. The collected spectral response may be used to determine whether each region of interest of the blood vessel wall 104 comprises a lipid pool or lipid-rich atheroma, a disrupted plaque, a vulnerable plaque or thin-cap fibroatheroma (TCFA), a fibrotic lesion, a calcific lesion, and/or normal tissue as described in U.S. Pat. Publ. Nos. US 2004/0024298-A1 and US-2005/0228295-A1, which are incorporated herein by this reference in their entirety.

FIGS. 3-7 illustrate different embodiments of the pullback and rotation unit 105 and a console 106 and how components of the optical subsystem 310, IVUS subsystem 312, and computer 117 are distributed between the pullback and rotation unit 105 and console 106.

Figure 3:
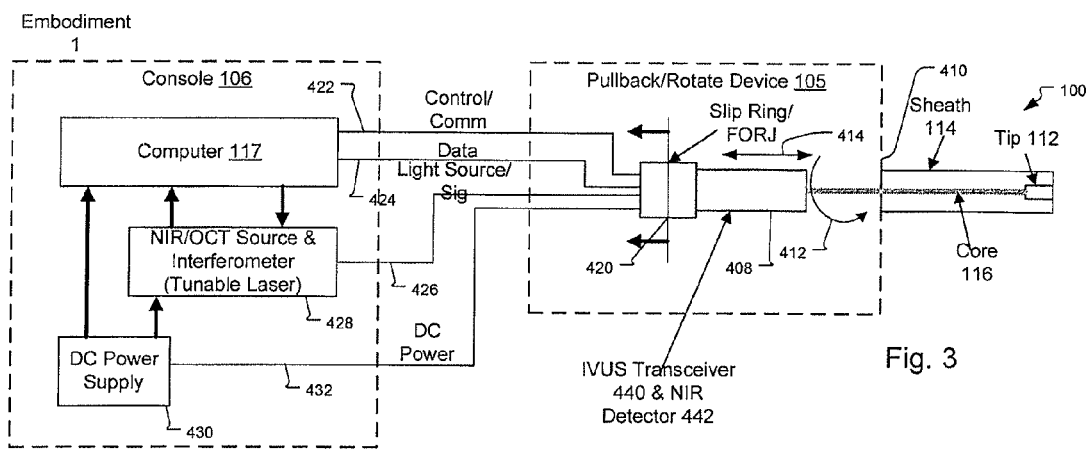
FIGS. 3-7 are schematic diagrams illustrating embodiments 1-5 having different component layouts between the pullback and rotation unit 105 and a console 106.

FIG. 3 illustrates embodiment 1. Like the other embodiments discussed below, the proximal portion of the catheter 100 connects or interfaces with the pullback and rotation unit 105. Specifically, the sheath 114 connects to the stationary housing 410 of the unit 105. The core 116 connects to a drum unit 408 that drives the rotation of the core 116, see arrow 412, and the longitudinal movement of the core 116 relative to the sheath 114, see arrow 414.

The drum 408 includes a slip ring/FORJ assembly 420 that couples electrical and optical signals between the rotating drum 408 and the stationary components of the console 106. The slip rings support the electrical connections and the FORJ supports one or more optical connects across the rotating interface. In more detail, control and communication electrical connections 422 are provided between computer 117 and the drum, along with data connections 424. Optical connections 426 are provided between the drum 408 and an NIR/OCT source and interferometer unit 428 of the optical subsystem 310. Finally, power is provided to the drum 408 by a D.C. power supply 430 on connection 432.

The computer 117 also controls the NIR/OCT source and interferometer unit 428 of the console. The power supply 430 powers the NIR/OCT source and interferometer unit 428 and the computer 117.

In embodiment 1, the components supporting the OCT analysis are provided in the NIR/OCT source and interferometer unit 428 of the console 106. This includes a tunable laser that tunes the scan band for the NIR analysis. The light returning on the collection fiber 123 of the catheter 100 is detected on a detector 442 of the optical subsystem 310 on drum 408. The electrical components of the IVUS system are similarly located on the drum 408, including the transceiver electronics 440 of the IVUS subsystem 312. The data generated by the IVUS analysis and the NIR analysis is transmitted electrically to the computer via the slip rings on connection 424.

The FORJ 420 connects the delivery fiber 122 of the catheter 100 to the OCT source and interferometer 428, which includes reference arm, a tunable laser, coupler/beamsplitter and an OCT detector such as a balanced detection system.

In the operation of embodiment 1, optical radiation in the near infrared (NIR) spectral regions is used for both the OCT and NIR analysis, being generated by the tunable laser of unit 428. Exemplary scan bands include 1000 to 1450 nanometers (nm) generally, or 1000 nm to 1350 nm, 1150 nm to 1250 nm, 1175 nm to 1280 nm, and 1190 nm to 1250 nm, more specifically. Other exemplary scan bands include 1660 nm to 1740 nm, and 1630 nm to 1800 nm.

Figure 4:
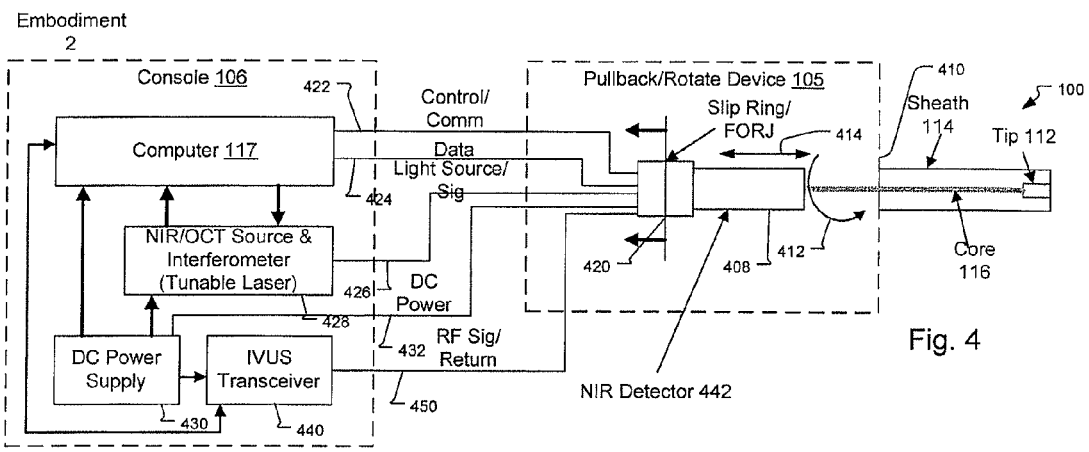

FIG. 4 shows embodiment 2, which differs from embodiment 1 in a number of respects. Specifically, in this embodiment, the IVUS transceiver 440 of the IVUS subsystem 312 is located on the console 106. Thus the slip ring electrical connections must support the transmission of radio frequency signals on connection 450 between the transceiver 440 and the drum 408. As a result, this embodiment would be compatible with the pullback and rotation unit described in incorporated application Ser. No. 12/062,188, with minor modifications to support the RF connections for the IVUS subsystem.

Figure 5:
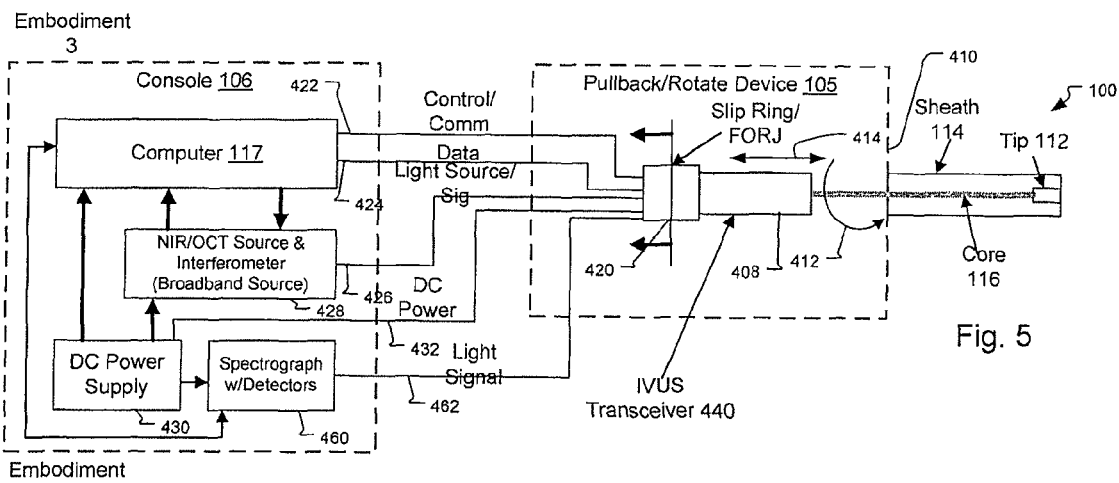

FIG. 5 shows embodiment 3, which differs from embodiment 1 in a number of respects. In this embodiment, the NIR/OCT source and interferometer unit 428 utilizes a broadband source, instead of the tunable laser embodiment 1. In a preferred embodiment, the source is a superluminescent light emitting diode (SLED).

Thus, to resolve the NIR spectral response of the vessels, a spectrometer spectrograph/detector system 460 is provided, in the console 106, in this example. This configuration of the optical subsystem 310 requires a two optical channel FORJ 420, channel 426 associated with the delivery fiber 122 and channel 462 associated with the collection optical fiber 123. Such dual channel FORJ components are offered, for example, by Princetel, Inc. (product number MS2-155-28).

The spectrograph 460 is preferably a high speed device to support high speed scanning of the vessel walls at about 300 frames/second, simultaneously with the OCT analysis, in some implementations. In one embodiment, an InGaAs detector array from Hamamatsu Photonics K.K. is used in combination with a Horiba Jobin Yvon Inc. grating, which disperses the spectrum over the detector array.

Figure 6:
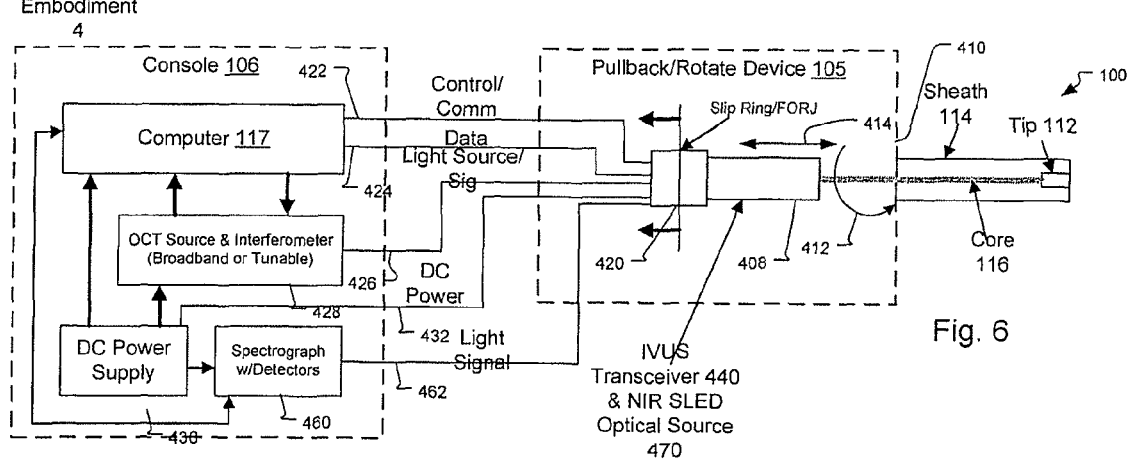

FIG. 6 shows embodiment 4 which differs from embodiment 3 in that the OCT source is not used for the NIR analysis. Specifically, in this example, an NIR SLED optical source 470 in provided on the drum 408. Light from the NIR source is combined with OCT light from the OCT source and interferometer unit 428 on a single delivery fiber, in one example, or two delivery fibers are provided in the catheter 100, in another example. Light returning on the collection fiber 123 is coupled off the drum 408 through a dual channel FORJ 420 to spectrograph 460. This system has advantages in that the source for the OCT and NIR can be individually optimized for each analysis, possibly operating at different wavelength scan speeds and in different scan bands.

Figure 7:
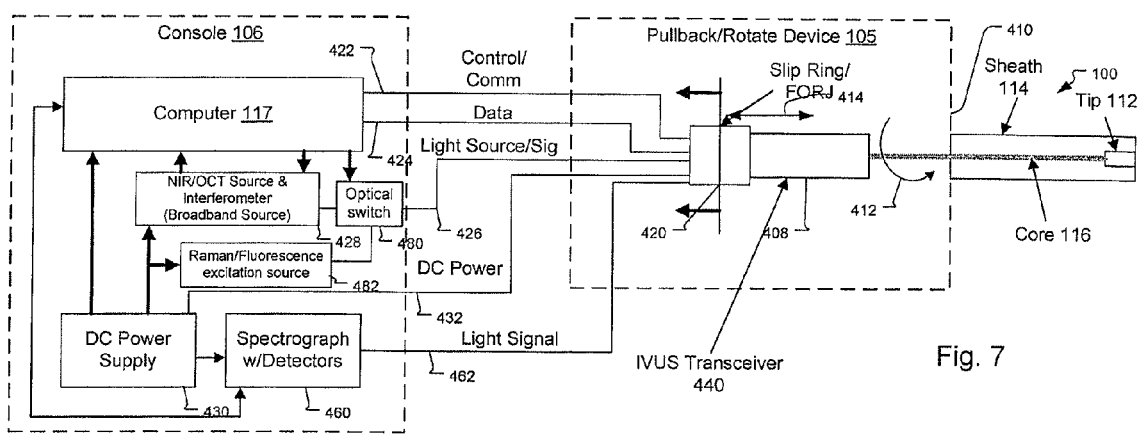

FIG. 7 shows embodiment 5, which is similar to embodiment 4, but includes the capability for Raman and/or fluorescence analysis. Specifically, it includes a Raman and fluorescence excitation source 482. The Raman/fluorescence laser source 482 is a relatively high power laser and is usually a single frequency laser or laser with only limited wavelength scanning. The Raman process is a weak and non-linear process. Thus, high excitation powers are preferably used, but below the damage threshold for the tissue of the vessel walls 104.

The light from this Raman source 482 is selectively coupled onto the delivery fiber via optical switch 480. In other examples, a wavelength multiplexer is used in place of the switch 482 when the optical bands of the OCT and NIR systems 428 do not overlap with the wavelength band of the light from the excitation source 482. Thus this embodiment adds Raman and/or fluorescence analysis to NIR and OCT modalities.

Serial/Simultaneous NIR/OCT/IVUS Scanning

Depending on the implementation, the IVUS information and the optical analysis information are produced during the same or different scans of the scanning catheter 112. For example, in one implementation, the optical information 410 produced by the NIR and OCT analysis, and IVUS information produced by the IVUS analysis, are captured simultaneously while withdrawing and rotating the scanning catheter 112 through the blood vessels 104, in the same pullback cycle of the pullback and rotation unit 105. In other implementations, the optical information 410 produced by the NIR analysis and IVUS information produced by the IVUS subsystem are captured during the same pullback and rotation operations of the scanning catheter 112 but the OCT analysis is performed in its own dedicated pullback cycle. Then the optical information data set produced by the NIR analysis and IVUS data set are spatially aligned with the OCT data set, with respect to each other. This alignment further includes compensation for the offset distance D (offset) between the IVUS transducer 120 and the optical bench 118, see FIG. 1.

In a serial scan implementation protocol, the NIR analysis is first performed over the entire length of the artery of interest. This leverages an advantage of the NIR analysis: neither occlusion nor a saline flush is necessary since the analysis can be performed through the flowing blood. This initial NIR analysis is used to identify regions of the artery that require further analysis via OCT. Another advantage associated with serial scanning arises from the fact that the OCT analysis is typically performed at higher scanning speeds in terms of the rotation speed of the catheter and the rate of pullback through the artery. Thus when NIR and OCT are performed during separate scans, optimal speeds can be used for both modalities. Another advantage is that the OCT is performed only at selected locations and thus the length of time and volume of the concomitant saline flush is minimized and kept within clinically appropriate limits.

Also, any IVUS scan typically takes longer than the OCT scan since it uses slower rotation speeds and pullback speeds than the OCT. Generally, the OCT scan is completed with about 4-5 seconds, which is the window provided by a 20 cc saline flush.

Despite the fact that some implementations employ separate scans for the NIR, OCT and IVUS analyses, the disclosed system provides advantages in that only a single catheter must be inserted in the patient, decreasing risk to the patient and lowering the time required for the invasive portions of the procedure.

A final key consideration in the "fusing" of image data obtained from different modalities (e.g. angiography, NIR, OCT, IVUS) is the accurate spatial co-registration (longitudinal and rotational) of the images. Having one catheter that incorporates multiple invasive imaging modalities provides a fixed frame of reference that greatly facilitates co-registration. This registration is further improved by using the position detection system including the internal element 150 and external element 152.

Thus, exemplary embodiments have been fully described above with reference to the drawing figures. Although the invention has been described based upon these exemplary embodiments, it would be apparent to those of skill in the art that certain modifications, variations, and alternative constructions could be made to the described embodiments within the spirit and scope of the invention.

We claim:

1. An intravascular catheter system comprising:
a catheter comprising:
at least one optical fiber configured to transmit optical radiation between distal and proximal ends thereof,
an optical bench disposed at the distal end of said optical fiber and configured to direct light transmitted from said optical fiber to an arterial wall and to direct light scattered or reflected by the arterial wall into said optical fiber; and
an ultrasound transducer configured to transmit ultrasound energy toward the arterial wall, receive ultrasound energy reflected from the arterial wall, and convert the received ultrasound energy to an electric signal a pull back and rotation system operatively coupled to said catheter and configured to impart rotational movement of said catheter about a longitudinal axis of said catheter and axial movement of said catheter along the longitudinal axis of said catheter;

a slip ring/ fiber optic rotary joint (FORJ) assembly including a rotating portion coupled to said catheter and a non-rotating portion and configured to couple electrical signals and optical signals between said rotating and non-rotating portions thereof;

at least one non-rotating source of optical radiation optically coupled to a portion of said optical fiber through said slip ring/FORJ assembly and configured to generate optical radiation to be transmitted by said optical fiber to the arterial wall through said optical bench;

an optical detector disposed on the rotating portion of said slip ring/FORJ assembly and optically coupled to said optical fiber and configured to receive optical radiation transmitted by said optical fiber from the arterial wall and convert the received optical signals to electrical signals that are transmitted over said slip ring/FORJ assembly to a computer to provide spectroscopic data about the arterial wall;

an ultrasound transceiver coupled to said ultrasound transducer and including drive electronics for driving said ultrasound transducer and configured to receive response signals from said ultrasound transducer and convert the received response signals to electronic signals that are transmitted to a computer to provide ultrasound image data for the arterial wall;

a non-rotating interferometer optically coupled to said optical fiber via said slip ring/FORJ assembly and configured to receive optical radiation transmitted by said optical fiber from the arterial wall and to provide an interference signal for sub-surface image data for the arterial wall; and a user interface configured to present one or more representations of the morphological and chemical structure of the arterial walls based on the spectroscopic data from said optical detector, the ultrasound image data from said ultrasound transceiver, and sub-surface image data from said interferometer.

2. The intravascular catheter system of claim 1, wherein said at least one optical fiber comprises a delivery fiber and a collection fiber and wherein said at least one source is optically coupled with a portion of said delivery fiber, said interferometer is optically coupled to a portion of said delivery fiber and configured to receive optical radiation transmitted by said delivery fiber from the arterial wall, and said optical detector is optically coupled to a portion of said collection fiber and configured to receive optical radiation transmitted by said collection fiber from the arterial wall.

3. The intravascular catheter system of claim 2, wherein said delivery fiber is a single mode optical fiber configured to propagate only a single spatial mode and said collection fiber comprises a multimode fiber.

4. The intravascular catheter system of claim 1, wherein said optical bench comprises at least one reflector configured to redirect optical radiation from said distal end of said optical fiber toward the arterial wall and to redirect at least a portion of the optical radiation from the arterial wall toward said distal end of said fiber.

5. The intravascular catheter system of claim 1, wherein said at least one optical radiation source comprises one or both of a tunable laser and a super luminescent light emitting diode.

6. The intravascular catheter system of claim 1, wherein said ultrasound transducer is configured to employ time multiplexing to both transmit ultrasound energy toward the arterial wall and receive ultrasound energy from the arterial wall.

7. The intravascular catheter system of claim 1, further comprising one or more wires providing an electrical connection between said ultrasound transducer and said ultrasonic subsystem.

8. The intravascular catheter system of claim 1, wherein said catheter comprises an outer sheath covering at least a portion of said optical fiber.

9. The intravascular catheter system of claim 8, further comprising a guide wire coupled to a portion of said sheath and configured to guide movement of said sheath and said optical fiber through an intravascular lumen.

10. The intravascular catheter system of claim 1, further comprising a position detection system comprising an internal element configured to be inserted into an intravascular lumen along with said optical fiber and an external element disposed outside the intravascular lumen, wherein said internal element and said external element are configured for communication therebetween for locating a position of said internal element relative to said external element.

11. The intravascular catheter system of claim 1, wherein said at least one optical fiber and said ultrasound transducer comprise a catheter core, and wherein said system further comprises a torque cable coupled to said catheter core and configured to transmit a rotational force to a distal portion of said catheter core.

12. The intravascular catheter system of claim 1, wherein said ultrasound transducer is distally spaced from said distal end of said optical fiber.

13. The intravascular catheter system of claim 1, wherein said ultrasound transceiver is non-rotating.

14. The intravascular catheter system of claim 1, wherein said ultrasound transceiver is disposed on the rotating portion of said slip ring/FORJ assembly the electronic signals are transmitted over said slip ring/FORJ assembly from said ultrasound transceiver to the computer.

* * * * *